United States Patent
Ekin et al.

(10) Patent No.: US 12,082,889 B2
(45) Date of Patent: Sep. 10, 2024

(54) GENERATING INTERACTIVE ZONES FOR INTERVENTIONAL MEDICAL DEVICES

(71) Applicant: KONINKLIJKE PHILIPS N.V., Eindhoven (NL)

(72) Inventors: Ahmet Ekin, Eindhoven (NL); Wilhelmus Henrica Gerarda Maria Van Den Boomen, Valkenswaard (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 17/786,575

(22) PCT Filed: Dec. 9, 2020

(86) PCT No.: PCT/EP2020/085151
§ 371 (c)(1),
(2) Date: Jun. 17, 2022

(87) PCT Pub. No.: WO2021/122181
PCT Pub. Date: Jun. 24, 2021

(65) Prior Publication Data
US 2023/0127144 A1    Apr. 27, 2023

(30) Foreign Application Priority Data
Dec. 20, 2019    (EP) .................................. 19218888

(51) Int. Cl.
*G06F 3/048*    (2013.01)
*A61B 34/00*    (2016.01)
(Continued)

(52) U.S. Cl.
CPC .............. *A61B 34/25* (2016.02); *A61B 34/10* (2016.02); *A61B 90/90* (2016.02); *G06F 3/0481* (2013.01);
(Continued)

(58) Field of Classification Search
CPC ......... A61B 34/25; A61B 34/10; A61B 90/90; A61B 2034/102; G06T 7/73;
(Continued)

(56) References Cited

U.S. PATENT DOCUMENTS 10,762,636 B2 *    9/2020    Gering ................ G06F 18/2115
11,684,348 B1 *    6/2023    Poplaw ............. A61M 25/0606
                                                              600/567
(Continued)

FOREIGN PATENT DOCUMENTS

WO    2004070604 A2    8/2004
WO    2015049142 A1    4/2015
(Continued)

OTHER PUBLICATIONS

International Search Report and Written Opinion of PCT/EP2020/085151, dated Mar. 5, 2021.
(Continued)

*Primary Examiner* — David Phantana-angkool

(57) ABSTRACT

A concept for facilitating a user interface for interacting with interventional medical devices depicted in an image. The positions of one or more features of at least one interventional medical device are identified. A size and shape of an interactive zone is determined for each feature, where an interactive zone (when provided on a display of a user interface) facilitates interaction with the corresponding feature and/or interventional medical device. The size of the interactive zone is chosen to be larger than the size of the feature. A position for the interactive zone is selected based on the position/position of the corresponding feature in the image. Zone information is then output to define the size, shape and position of the interactive zones with respect to the image.

20 Claims, 4 Drawing Sheets

(51) Int. Cl.
*A61B 34/10* (2016.01)
*A61B 90/90* (2016.01)
*G06F 3/0481* (2022.01)
*G06F 3/04842* (2022.01)
*G06T 7/73* (2017.01)

(52) U.S. Cl.
CPC ............ *G06F 3/04842* (2013.01); *G06T 7/73* (2017.01); *A61B 2034/102* (2016.02); *G06T 2200/24* (2013.01); *G06T 2207/30004* (2013.01)

(58) Field of Classification Search
CPC ....... G06T 2200/24; G06T 2207/30004; G06F 3/0481; G06F 3/04842
See application file for complete search history.

(56) References Cited

U.S. PATENT DOCUMENTS

| | | | |
|---|---|---|---|
| 2016/0081760 A1 | 3/2016 | Verard | |
| 2017/0235582 A1* | 8/2017 | Ramirez | G06F 3/04842 715/708 |
| 2017/0358091 A1 | 12/2017 | Ekin | |
| 2018/0042680 A1 | 2/2018 | Dimaio | |
| 2020/0143934 A1* | 5/2020 | Gering | G16H 30/40 |
| 2020/0364874 A1* | 11/2020 | Gering | G06T 7/0012 |
| 2021/0264589 A1* | 8/2021 | Jacob | G06N 3/047 |
| 2022/0101034 A1* | 3/2022 | Ekin | G06T 7/11 |
| 2023/0127144 A1* | 4/2023 | Ekin | A61B 90/90 715/771 |

FOREIGN PATENT DOCUMENTS

| | | |
|---|---|---|
| WO | 2016041793 A1 | 3/2016 |
| WO | 2018178248 A1 | 10/2018 |
| WO | 2018195216 A1 | 10/2018 |

OTHER PUBLICATIONS

Osga, Glenn A. "Using Enlarged Target Area and Constant Visual Feedback to Aid Cursor Pointing Tasks", Proceedings of the Human Factors Society 35th Annual Meeting—1991.

Shadeed, Ahmad, "Enhancing the Clickable Area Size", Aug. 2019.

* cited by examiner

GENERATING INTERACTIVE ZONES FOR INTERVENTIONAL MEDICAL DEVICES

CROSS-REFERENCE TO PRIOR APPLICATIONS

This application is the U.S. National Phase application under 35 U.S.C. §371 of International Application No. PCT/EP2020/085181, filed on Dec. 9, 2020, which claims the benefit of European Patent Application No. 19218888.6, filed on Dec. 20, 2019. These applications are hereby incorporated by reference herein.

FIELD OF THE INVENTION

The present invention relates to the field of user interfaces, and in particular to user interfaces providing an interactive image.

BACKGROUND OF THE INVENTION

Standard user interfaces often require the user to operate a user input device, such as a mouse, to interact or click on devices/elements in an image.

User interfaces are becoming increasingly used in clinical interventional procedures, to guide, tune and/or visualize an interventional medical device throughout the procedure. In such embodiments, the user may interact with the user interface in order to modify parameters of the interventional medical device, visualize the interventional medical device and/or monitor the position/progress of the interventional medical device within a patient.

However, the process of operating the user input device to interact with the user interface tool can be inconvenient or bothersome for a clinician during a clinical intervention procedure. There is a desire to provide a user interface system that allows a user to more easily interact with a user interface with greater accuracy and/or precision.

SUMMARY OF THE INVENTION

The invention is defined by the claims.

According to examples in accordance with an aspect of the invention, there is provided a computer-implemented method for facilitating interaction with an interventional medical device in an image for display at a user interface.

The computer-implemented method comprises: obtaining the position of at least one feature of one or more interventional medical devices with respect to or within an image, like a two-dimensional (2D) image, for display at a user interface, like a two-dimensional (2D) user interface, containing a two-dimensional (2D) visual representation of each one or more interventional medical devices; performing a zone generation process comprising, for each of one or more features, determining a size and shape for an interactive zone for overlaying a portion of a displayed image on the user interface and with which the user is able to interact via the user interface, wherein the interactive zone has a size greater than the size of the feature associated with the interactive zone; determining, for each interactive zone, a position for the interactive zone relative to the image based on the position of the associated feature; and outputting zone information comprising at least information on the size, shape and position of each interactive zone. In particular, said 2D visual representation of the interventional device is a projection of the interventional device (which navigates inside the patient—in a 3D volume) onto the 2D surface of the image (or the screen—user interface).

The invention facilitates a new user interface for providing an improved user-machine interaction. The position of one or more interventional medical devices, such as a catheter, stent or guidewire, within an image is established. An interactive zone is generated for at least one feature of the interventional medical device(s), each interactive zone defining an area of a display of the user interface with which a user is able to interact (e.g. click or select). Information on the interactive zones is output as zone information, to allow a user interface to display the image and the interactive zones. The method thereby facilitates a new user interface, having interactive zones larger than the feature of an interventional medical device with which a user may wish to interact.

By defining the size of the interactive zones to be larger than the size of the feature to which they correspond, the proposed concept enables simpler selection of and/or interaction with feature(s) of an interventional medical device within an image. In particular, the concept reduces the need for a user to carefully select the precise position and position of the (features of the) interventional medical device when interacting with the image, thereby providing a simpler, quicker and more easy-to-use user interface. The proposed concept may also be more intuitive in use.

The present invention is particularly advantageous when the interventional medical devices are elongate interventional medical devices. This is because interacting with elongate interventional medical devices, such as guidewires or catheters, in an image is particularly cumbersome and/or tricky due to the precision required to interact with such elongate devices. By providing a larger interactive zone (i.e. larger than (a feature of) the elongate interventional medical device), the necessary precision is reduced, thereby increasing an ease with which a user can interact with the (feature of the) elongate interventional medical device.

The step of determining, for each interactive zone, a position of the interactive zone may comprise determining, for each interactive zone, the position of the interactive zone so that the interactive zone overlaps at least a portion of the feature associated with the interactive zone.

In some embodiments, at least one feature comprises the entirety of an interventional medical device.

In some embodiments, the step of determining a shape of an interactive zone comprises setting the shape of the interactive zone to be the same as the shape of the feature associated with the interactive zone.

The step of obtaining the position of at least one feature may comprise processing the image to identify the position of at least one feature of the one or more interventional medical devices.

Other embodiments for obtaining the position of at least one feature will be apparent to the skilled person. For example, an external source may provide information on the position of at least one feature within the image. Suitable examples of an external source include: an image processor (that pre-processes the image to identify the one or more features) or shape sensing data provider, such as an optical sensor for the interventional medical device, or a combination of the foregoing.

Methods of processing an image to identify the position of at least one feature will be apparent to the skilled person, and may comprise, for example, segmenting the image using one or more deep learning or image analysis methods.

Optionally, the step of generating an interactive zone comprises determining at least one visual display property for the interactive zone, wherein the zone information further comprises information on the determined at least one visual display property for each interactive zone. Each interactive zone preferably has at least one unique visual display property. This increases an ease with which a user can distinguish between different interactive zones and therefore different interventional medical devices.

By way of example, a visual display property may comprise a color, shade, opacity and/or pattern fill for the interactive zone.

Embodiments may further comprise a step of obtaining identifying information identifying a type of each interventional medical device, wherein each interactive zone shares a common display property as any other interactive zone associated with a feature of an interventional medical device of the same type, wherein the said display property is different for any interactive zone corresponding to an interventional medical device of a different type.

This embodiment enables a user to more readily identify different types of interventional medical devices and their associated zones, e.g. to enable a user to more quickly establish all interventional medical devices of a particular type by looking for a common display property.

The type may device may comprise, for example, an identity and/or category of an interventional medical device. By way of example, devices may be divisible into two categories: shape-sensed devices or non-shape-sensed devices. In another example, devices may be divisible into two other categories: stationary and non-stationary. In yet another example, devices can be divided into categories based on their size and/or thickness (e.g. devices below 10 mm and devices greater than 10 mm in thickness). Of course, a type of device may comprise any combination of the foregoing (e.g. a type may be stationary devices less than 10 mm in thickness).

Optionally, the size of each interactive zone is responsive to the number of) at least one) features upon which a zone generation process is performed in the image.

In some embodiments, the method further comprises a step of obtaining identifying information identifying a type of each interventional medical device, wherein: the zone generation process comprises receiving a user input identifying one or more desired types of interventional medical device and only generating an interactive zone for at least one feature of interventional medical devices of the one or more desired types.

Thus, a user may restrict the generated zones to include only those of a particular type. This increases an ease of the user for selecting a desired interventional medical device (by limiting the zones that are generated to a desired type matching the desired interventional medical device).

Preferably, all interactive zones are sized, shaped and/or positioned to prevent an overlap between different interactive zones. Thus, the space occupied by a zone may depend upon how many zones are generated. This enables, for example, larger zones if there are fewer interventional medical devices, to reduce the likelihood of a user mis-selecting or mis-clicking on an undesired zone.

The image comprises data obtained from a medical image, such as an X-ray image, a CT image, an ultrasound and so on.

There is also proposed a computer program product comprising a computer readable storage medium having computer readable program instructions thereon for causing a processing system to implement any herein described method when said computer readable program instructions are executed by the processing system.

There is also proposed an interactive zone processing unit for facilitating interaction with an interventional medical device in an image for display at a user interface.

The interactive zone processing unit is adapted to: obtain the position of at least one feature of one or more interventional medical devices with respect to an image, for display at a user interface, containing a visual representation of each one or more interventional medical devices; perform a zone generation process comprising, for each of one or more features, determining a size and shape for an interactive zone for overlaying a portion of a displayed image on the user interface and with which the user is able to interact via the user interface, wherein the interactive zone has a size greater than the size of the feature associated with the interactive zone; determine, for each interactive zone, a position for the interactive zone relative to the image based on the position of the associated feature; and output zone information comprising at least information on the size, shape and position of each interactive zone.

Some embodiments provide a user interface system comprising a user interface, and a processor. The processor comprises a user interface processing unit and the interactive zone processing unit. The user interface processing unit is adapted to obtain the image and the zone information, and control the user interface to provide an interactive image based on the obtained image and zone information.

The user interface processing unit may respond to a user interaction, via the user interface, with an interactive zone by performing one or more predefined actions.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
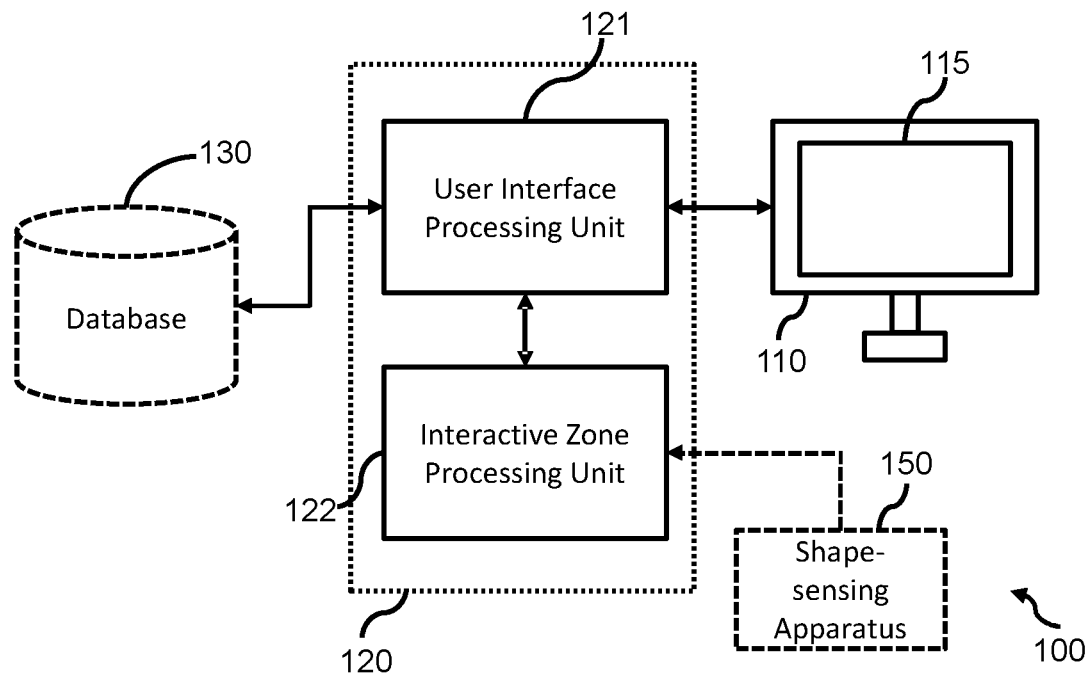
FIG. 1 illustrates a user interface system according to an embodiment of the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a concept for facilitating a user interface for interacting with interventional medical devices depicted in an image. The positions of one or more features of at least one interventional medical device are obtained. A size and shape of an interactive zone is determined for each feature, where an interactive zone (when provided on a display of a user interface) facilitates interaction with the corresponding feature and/or interventional medical device. The size of the interactive zone is chosen to be larger than the size of the feature. A position for the interactive zone is selected based on the position/position of the corresponding feature in the image. Zone information is then output to define the size, shape and position of the interactive zones with respect to the image.

Embodiments are based on the realization that interacting with a display of (features of) an interventional medical device is difficult to perform with precision, especially during an interventional clinical procedure, due to the small size of the interventional medical devices and the difficulty in manipulating an interventional medical device whilst interacting with a user interface. It has been recognized that the required precision (of a user) can be reduced by sizing interactive zones to be larger than the size of the feature of the interventional medical device, thereby providing a better user interface for facilitating human-machine interaction.

The invention may be employed in any clinical environment in which interventional medical devices are used, such as in an operating room or intensive care unit.

In the context of the present invention, a feature may comprise the entire interventional medical device or a portion of the interventional medical device, such as a landmark, tip or component part of the interventional medical device. Thus, interaction with an interactive zone may facilitate interaction with the overall interventional medical device and/or a portion thereof.

FIG. 1 illustrates a user interface system 100 according to an embodiment of the invention. The user interface system comprises a user interface 110, a processor 120 and a (optional) database 130.

The user interface system may be part of an overall medical system for use with an interventional (medical/clinical) device. In particular, the user interface system may allow the user to visualize an interventional medical device and/or control parameters of the interventional medical device, its environment and/or the visualization of the interventional medical device.

The user interface 110 is adapted to display, e.g. at a two-dimensional screen 115, an interactive image. Interaction with the interactive image may be via touch (e.g. if the two-dimensional screen is a touch-sensitive screen), via a voice input or any other input mechanism (e.g. mouse or keyboard inputs). Thus, the user interface 110 may comprise an input mechanism for enabling a user to interact with the interactive image.

In the present invention, an interactive image is formed in two aspects: an image (i.e. providing visual information about a subject, in particular providing a visual representation of an interventional medical device) and one or more interactive zones overlaying (portions of) the image with which a user can interact.

The image may comprise data obtained from a medical image, such as an X-ray image, CT image, an MRI image and so on. In some embodiments, the interventional medical device is depicted within the medical image itself.

In some embodiments, the visual representation of the medical device is obtained from an device positioning system, e.g. an optical fiber connected to the medical device, that can be used to identify the position of the medical device (with respect to an image or display) and be used to generate a visual representation of the interventional medical device on a displayed image. This could be represented upon a default or model image of a human anatomy.

In some embodiments, the displayed image is a combination of both, e.g. an underlying medical image of the subject with a visual representation of an interventional medical device overlaying the underlying medical image indicating its position with respect to the subject. This embodiment is not essential, and the displayed image may instead consist, for example, of the medical image alone.

The processor 120 is adapted to control the interactive image displayed by the user interface, and respond to any user interaction with the interactive image. In particular, a user interface processing unit or module 121 obtains the image for display, e.g. from the database 130 or directly from an image generating device (such as an X-ray system and/or device positioning system), and responds to user interactions at the user interface 110 to perform actions (e.g. controlling external devices and/or controlling a display of the interactive image).

An interactive zone processing unit 122 generates the interactive zones for the image. An interactive zone defines positions and/or areas of the interactive image with which the user is able to interact, to cause a certain action or actions to be performed. In particular, an interactive zone overlays a portion of the image to thereby provide an interactive area of the image. The interactive zone may have a visual representation (e.g., a particular shading, color, outline opacity and/or pattern fill) or may be transparent/non-visible. Different types of interactions (e.g. a tap or a long press) with an interactive zone may trigger different actions.

The displayed interactive image comprises one or more interventional medical devices, such as those used in invasive clinical procedures. Each interactive zone represents a feature of the interventional medical device(s). An interactive zone may effectively enable a user to interact with the corresponding feature of the interventional medical device(s) and/or the corresponding interventional medical device itself.

A general process for providing an interactive image is hereafter provided for the purposes of improved contextual understanding of the invention. However, embodiments are not limited to the precise steps performed in this process.

In this general process, the user interface processing unit 121 of the processor 120 obtains a (non-interactive) image for display at the user interface 115, e.g. from a database 130. The obtained image is of one or more interventional medical devices. The interactive zone processing unit 122 of the processor 120 generates, for the obtained image, one or more interactive zones for at least one feature of the interventional medical device(s), such as a landmark of an interventional medical device or an entire interventional medical device itself. The interactive zone processing unit 122 generates information on the generated interactive zones (e.g. at least their size, shape and position relative to the image) and outputs this information as zone information. The user interface processing unit 121 obtains the zone information from the interactive processing unit 122, and controls the user interface 110 to provide an interactive image based on the obtained image and the zone information.

Subsequent interaction, by a user, with the interactive image via the user interface 110 can trigger one or more actions. For example, a first interaction with an interactive zone may cause the user interface to "zoom in" on a feature associated with the interactive zone. A second, different interaction with an interactive zone may cause the feature associated with the interactive zone to be highlighted, e.g.

for ease of viewing. Different actions may be performed based upon the interactive zone selected and/or the type of interaction, such as an interaction pattern, e.g. long press, short tap or double tap.

The skilled person will appreciate that these possible actions are only examples, and would be able to implement any possible reaction to an interaction with an interactive zone. Further examples will be provided later in the description.

The present invention relates to the process of generating the interactive zones for the image, to thereby facilitate interaction with the interactive image and/or (features of the) interventional medical devices depicted within the image. Thus, the interactive zone processing unit 121 may itself be an embodiment of the invention.

An underlying concept of the present invention is that the size of the generated interactive zones are larger than the size of the feature that they represent. This facilitates easier interaction with the interactive image and/or the (features of the) interventional medical devices depicted within the image.

The present invention is particularly advantageous when the interventional medical devices are elongate interventional medical devices. This is because interacting with elongate interventional medical devices, such as guidewires or catheters, in an image is particularly cumbersome and/or tricky due to the precision required to interact with such elongate devices. By providing a larger interactive zone (i.e. larger than (a feature of) the elongate interventional medical device), the necessary precision is reduced, thereby increasing an ease with which a user can interact with the (feature of the) elongate interventional medical device.

Figure 2:
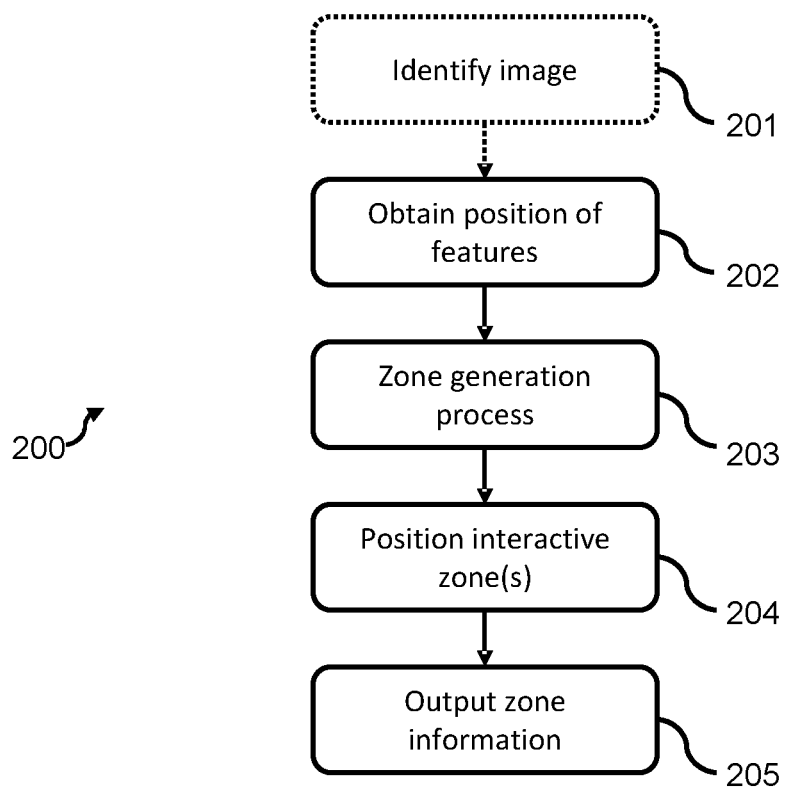
FIG. 2 illustrates a method according to an embodiment of the invention.

FIG. 2 illustrates a method 200 according to an embodiment of the invention. The method 200 may be performed by the interactive processing unit 121.

The method 200 comprises a step 202 of obtaining the position of at least one feature of one or more interventional medical devices with respect to an image, for display at a user interface, containing a visual representation of each one or more interventional medical devices. The position of the feature(s) (within the image) can be derived in a number of ways.

Suitable examples for the image may comprise data on an X-ray image, an ultrasound image, a CT image and so on. The image for display depicts one or more interventional medical devices. These may be represented as physical entities within the image.

As previously noted, a feature may comprise an entire interventional medical device or a portion of an interventional medical device, such as a landmark, tip or component part of the interventional medical device.

In some examples, the position of a feature is determined by processing the image using a machine-learning algorithm or other image analysis methodology, such as an image-segmentation technique. These examples enable the position and optionally identity of a feature to be established directly from the image.

In other examples, the position of a feature is provided by an external source, e.g. an external image analysis unit, or from shape sensing apparatus 150 (e.g. adapted to physically track a position of an interventional medical device with respect to an imaging device that captures the image). A suitable example of a shape sensing apparatus is an optical fiber coupled to an interventional medical device, which provides optical shape sensing information that can overlay the image.

In some embodiments, multiple possible positions for a feature may be identified, e.g. using a machine-learning method. An interactive zone may be generated, as later described, for each possible position to allow a user to select a correct position of the feature.

Of course, a combination of the foregoing approaches (i.e. a hybrid approach) may be used, e.g. using external data to identify a general position and performing image analysis to identify a precise position). Other methods of determining the position of a feature of an interventional medical device within an image would be apparent to the skilled person. Step 202 may, in some embodiments, be combined into step 201, so that identifying an image comprises obtaining information about a position of features within an image.

The method 200 further comprises a step 203 of performing a zone generation process. This process comprises, for each of one or more features, determining (at least) a size and shape for an interactive zone. As previously discussed, the interactive zone is for overlaying a (portion of a) displayed image on the user interface and can enable a user to interact, with the image and/or the (features of the) interventional medical devices depicted within the image, via the user interface.

The size of each interactive zone (relative to the image) is configured to be larger than the feature associated with the interactive zone, the "associated feature". The size of a zone or feature may be defined by the area of the image occupied by the said zone or feature.

The size of a feature may be determined, for example, during step 202 when an image undergoes an image analysis methodology. Other methods of determining a size of a feature will be apparent to the skilled person, for example, based on known sizes of a feature (e.g. a known size of an interventional medical device).

The method further comprises a step 204 of determining, for each interactive zone, a position for the interactive zone relative to the image based on the position of the feature associated with the interactive zone (i.e. the "associated feature").

The position may be defined, for example, as co-ordinates for the placement of the interactive zone within the image or a relative location (e.g. "upper left"). In some examples, the position may be defined relative to the corresponding feature (e.g. 10 pixels to the right of the feature or at the position of the feature).

Preferably, the position of each interactive zone is configured so that each interactive zone overlaps at least a portion of the feature with which it is associated. This embodiment enables an interactive zone to be graphically associated with a feature in an intuitive and clear manner, whilst maximizing the available space in the interactive image for providing an interactive zone.

Effectively, steps 203 and 204 together define the shape, size and position of interactive zones within the interactive image (which can be displayed/provided by a user interface). In particular, steps 203 and 204 define the shape, size and position of interactive zones with respect to, i.e. relative to, the image. This may be performed, for example, by determining pixel co-ordinates for the position of a zone within an image or determining any other information on where an interactive zone should be positioned relative to an image, e.g. "upper-left quadrant" or "lower half".

The shape of the interactive zone could be selected or determined in a number of ways.

For example, the shape of the interactive zone could be controlled based on the shape of the feature corresponding to the interactive zone (e.g. to match the shape of the feature). This aids a user in intuitively understanding to which feature the interactive zone corresponds.

In another example, the shape of the interactive zone is pre-determined (e.g. square, rectangular, circular, triangular etc.). In yet other examples, the shape of the interactive zone is controllable by a user, e.g. is responsive to a user input. In yet other examples, the shape of the interactive zone is dependent upon the number (and/or position) of interactives zones generated, e.g. to prevent interactive zones from overlapping.

Other embodiments will be apparent to the skilled person, so that defining the shape is not limited to any specific herein described example.

In preferable examples, the size and/or shape of each interactive zone is configured so that the interactive zone has a width/thickness greater than the feature of the interventional medical device with which it corresponds. This increases an ease with which a user is able to interact with the said feature (e.g. compared to embodiments in which the width/thickness of the interactive zone is the same as the feature of the interventional medical device).

Preferably, the size, shape and/or position of each interactive zone is configured so that the interactive zones do not overlap one another. This helps avoid confusion as to which interactive zone is associated with which feature.

Preferably, the size, shape and/or position of each interactive zone is configured so that the area of the interactive image occupied by the interactive zone(s) is greater than a half, for example, greater than ¾ of the overall image, for example the entire image. Thus, the space occupied by the interactive zones may be maximized.

Preferably, the size (and optionally shape and/or position) of each interactive zone is configured to maximize the average size of the interactive zones whilst aiming to minimize the range in sizes of the interactive zones. This embodiment is particularly preferred when the size, shape and/or position of each interactive zone is configured so that the interactive zones do not overlap one another.

The size, shape and/or position of each interactive zone may be controlled based on the number of (at least one) features upon which a zone generation process is performed. For example, the greater the number of features, the smaller the size of the interactive zone.

Preferably, the interactive zones may be sized, shaped and/or positioned so that they are arranged with respect to the image to maximize the size of each interactive zone whilst avoiding overlap of the interactive zones. In further preferred examples, the interactive zones are also shaped so as to have a same shape (but different size) to the corresponding feature.

The foregoing embodiments for determining the size, shape and/or position effectively enable context-adaptive determination of the interactive zone(s).

The method 200 further comprises a step 205 of outputting zone information comprising at least information on the size, shape and position of each interactive zone.

In some examples, the zone information further identifies at least one visual display property of the interactive zone (e.g. a color, opacity, fill pattern, outline and so on). To this end, the zone generation process performed in step 203 may further comprise, for each located feature, defining one or more visual display properties (and/or values thereof) for the corresponding interactive zone. In some embodiments, each interactive zone may have at least one unique visual display property, to aid in distinguishing the interactive zones from one another.

In some embodiments, a user may be able to define one or more of the display properties for the interactive zone. Thus, the zone information may identify at least one visual display property of the interactive zone based on a user input (e.g. received at the user interface), e.g. to define the color of a zone as pink, instead of yellow.

In some examples, the zone information further provides a (textual) label for each zone (e.g. "1" or "2"), which may be displayed alongside the interactive zone at the user interface. To this end, the zone generation process performed in step 203 may further comprise, for each located feature, generating at least one (textual) label for the corresponding interactive zone. The label for each interactive zone may be unique (for a particular interactive image). The labels could be later used to enable a user to interact with the interactive zone, e.g. using a voice command to interact with a particular interactive zone having a label.

The zone information can be used to control or define interactive zones of an interactive image. Thus, an interactive display may be controlled to provide interactive zones overlaying an image based on the zone information.

Some methods may further comprise a step of displaying the image and the interactive zones at a user interface, thereby providing an interactive image at the user interface. However, this is not essential to achieving the underlying concept of facilitating provision of interactives zones for an image.

Some methods may further comprise responding to interactions, performed by a user, with the interactive zone by performing one or more actions. Once again, this embodiment is not essential to the underlying concept.

Optionally, the method may comprise a step 201 of identifying a (medical) image, for display at a user interface, containing one or more interventional medical devices. The step 201 may comprise obtaining the image itself or simply obtaining information about the image comprising the interventional medical device(s).

FIGS. 3 to 6 are used to illustrate embodiments for defining the size, shape and position (i.e. zone information) of one or more interactive zones. This is illustrated graphically for the purposes of conceptual understanding, but the skilled person would appreciate that the process of generating the zone information does not need to be performed in a graphical manner.

Figure 3:
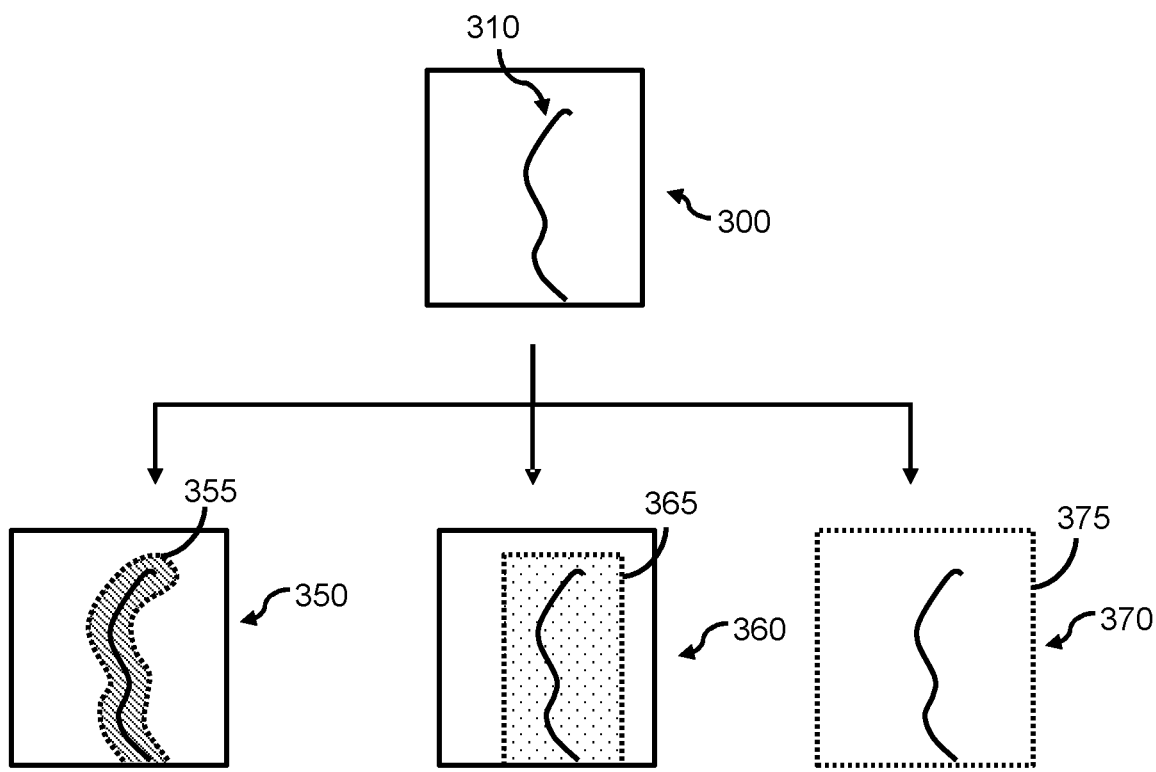
FIGS. 3 to 7 illustrates methods of generating an interactive zone according to different embodiments of the invention.

FIG. 3 conceptually illustrates various embodiments for generating an interactive zone for an image 300 of a single interventional medical device 310. This process may be performed by the interactive zone processing unit. Here, the interventional medical device 310 comprises a guidewire.

In particular, FIG. 3 conceptually illustrates different interactive images 350, 360, 370, in which the size, shape and position of interactive zones 355, 365, 375 is illustrated using dashed lines. Each interactive image 350, 360, 370 is the result of implementing a different embodiment or example of the invention.

In the illustrated example, each interactive zone 355, 365, 375 corresponds to a feature of the interventional medical device 310, which is here the entire interventional medical device. In other words, the feature of the interventional medical device is the shape and/or outline of the interventional medical device 310. Reference to an "interventional medical device" in the following passages may be replaced by the term a "feature of an interventional medical device" where appropriate for clarity.

In a first example, the image 300 is processed to generate a first interactive image 350, having a first interactive zone 355.

The size of the first interactive zone is configured to be greater than a size than the interventional medical device 355. For example, the size of the interactive zone may be configured to be a predetermined percentage or amount (e.g. number of pixels) larger than the size of the interventional medical device, or configured so that the thickness of the interactive zone is a predetermined amount (e.g. in number of pixels) thicker than the thickness of the interventional medical device) and so on.

The position of the first interactive zone 355 is dependent upon the position of the interventional medical device 355. Here, the first interactive zone is positioned to overlap the interventional medical device 355, and in particular, so that the interventional medical device is positioned in the middle/center of the interactive zone.

The first interactive zone 355 is shaped to be similar and/or identical to the shape of the interventional medical device 355. Thus, the shape of the first interactive zone is dependent upon the shape of the (feature of the) interventional medical device 355.

In a second example, the image 300 is processed to generate a second interactive image 360, having a second interactive zone 365. The second interactive zone 365 differs from the first interactive zone 355 in that the shape of the second interactive zone 365 is predetermined (here: a rectangle), and it not directly based on the shape of the interventional medical device.

In a third example, the image 300 is processed to generate a third interactive image 370, having a third interactive zone 375. The third interactive zone 375 is sized to occupy the whole image. This embodiment may only be possible if there is only a single (feature of) an interventional medical device in the interactive image.

As illustrated, to aid in identification of an interactive zone, the interactive zone may have at least one non-zero visual display property (e.g. be associated with a particular color, opacity, fill pattern, outline etc.).

Figure 4:
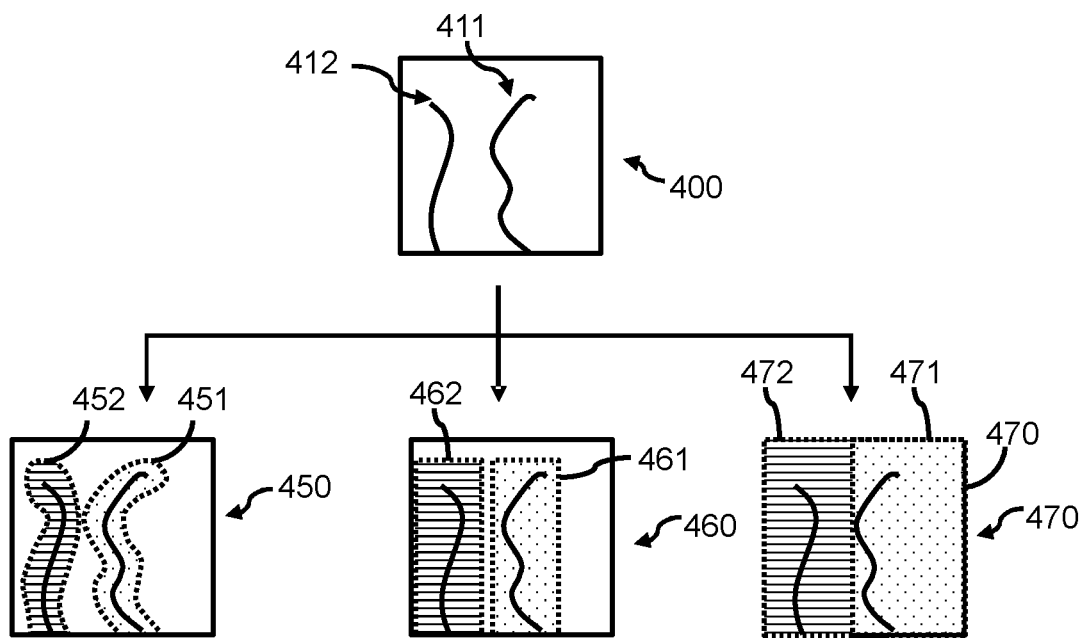

FIG. 4 conceptually illustrates further examples or embodiments for generating an interactive zone for an image 400. Here, the image 400 comprises a plurality of interventional medical device 411, 412, e.g. a plurality of guidewires.

In particular, FIG. 4 conceptually illustrates different interactive images 450, 460, 470, in which the size, shape and position of interactive zones 451, 452, 461, 462, 471, 472 is illustrated using dashed lines. Each interactive image 450, 460, 470 is the result of implementing a different embodiment or example of the invention.

As before, each interactive zone 451, 452, 461, 462, 471, 472 corresponds to a feature of the interventional medical device 411, 412, which is here the entire interventional medical device.

In a first example, the image 400 is processed to generate a first interactive image 450. The first interactive image 450 comprises a first 451 and second 452 interactive zone, each corresponding to a respective interventional medical device. In the first example, the shape of the interactive zones matches the shape of the corresponding interventional medical device.

In a second example, the image 400 is processed to generate a second interactive image 460. The second interactive image comprises a third 461 and fourth 462 interactive zone, each corresponding to a respective interventional medical device. The third and fourth interactive zones differ from the first and second interactive zones (respectively) in that the shape is independent of the shape of the corresponding interventional medical device.

In a third example, the image 400 is processed to generate a third interactive image 470. The third interactive image comprises a fifth 471 and sixth 472 interactive zone, each corresponding to a respective interventional medical device. The fifth and sixth interactive zones differ from the third and fourth interactive zones (respectively) in that the zones are sized so that they together fill the entire interactive image.

As illustrated in FIG. 4, to aid in identification of an interactive zone, the interactive zone may have at least one non-zero visual display property (e.g. be associated with a particular color, opacity, fill pattern, outline etc.). In particular, each interactive zone may have at least one unique visual display property, to distinguish the interactive zones from one another. In the illustrated example, each interactive zone has a different fill pattern.

Figure 5:
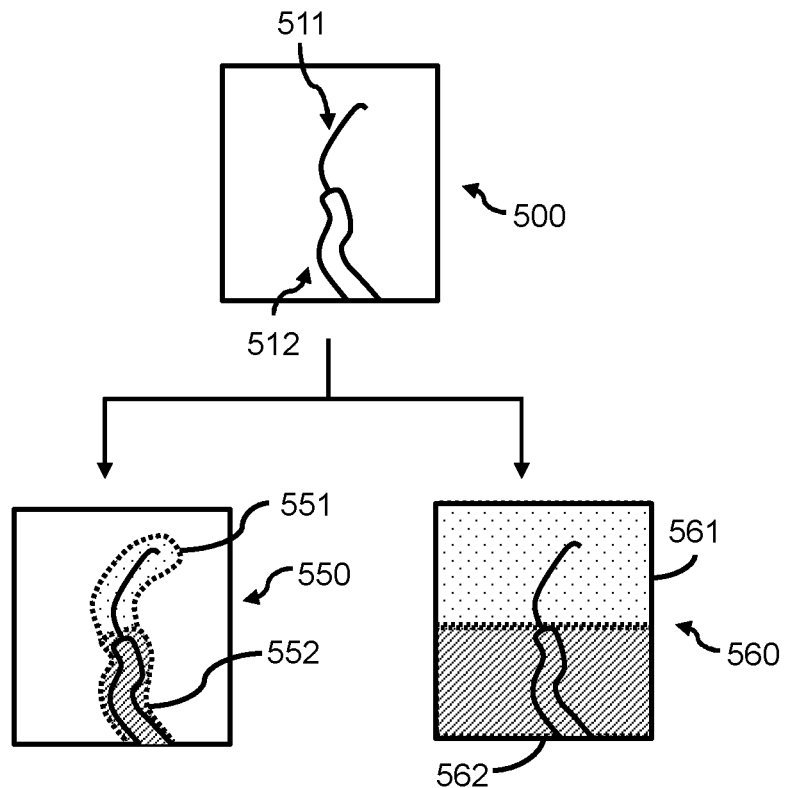

FIG. 5 conceptually illustrates further examples embodiments for generating an interactive zone for an image 500. Here, the image comprises a plurality of different types of interventional medical device 511, 512, e.g. a guidewire 511 and a catheter 512.

In particular, FIG. 5 conceptually illustrates different interactive images 550, 560, in which the size, shape and position of interactive zones 551, 552, 561, 562 is illustrated using dashed lines. Each interactive image 550, 560 is the result of implementing a different embodiment or example of the invention.

As before, each interactive zone 551, 552, 561, 562 corresponds to a feature of the interventional medical device 511, 512, which is here an interventional medical device itself.

In a first example, the image 500 is processed to generate a first interactive image 550. The first interactive image 550 comprises a first interactive zone 551 and a second interactive zone 552. The first interactive zone 551 corresponds to the guidewire 511 and the second interactive zone 552 corresponds to the catheter 512. Each interactive zone is shaped based on the shape of the interventional medical device with which it is associated.

In a second example, the image 500 is processed to generate a second interactive image 560. The second interactive image 560 comprises a third interactive zone 561 and a fourth interactive zone 562. The third interactive zone 561 corresponds to the guidewire 511 and the fourth interactive zone 562 corresponds to the catheter 512. The third and fourth interactive zones differ from the first and second interactive zones in that their shape is independent of the shape of the associated interventional medical device, and that they are sized to fill the interactive image.

As illustrated in FIGS. 3 to 5, in preferable examples the interactive zones are sized, shaped and positioned so that they do not overlap one another.

However, this is not essential, and the zones may be configured to at least partially overlap. In such embodiments, the user may (upon interacting with an overlapping zone) be asked to confirm which interactive zone they intend to interact with, e.g. through use of a pop-up menu or the like.

In the illustrated examples, each interactive zone is positioned so as to (when displayed with the corresponding image) overlap the feature with which it corresponds. However, whilst preferred, this is not an essential aspect of the invention.

Preferably, however, the interactive zone is at least configured to be graphically associated with the feature with which it corresponds. This may be performed, as previously illustrated, by positioning the interactive zone to overlap the feature.

In other examples, this is performed using graphical indicators or annotations, such as a callout or arrow identifying the feature corresponding to the interactive zone. In such examples, the zone information may contain information on the position, size and shape of such graphical indicators. Thus, the zone generation process may further comprise generating information on one or more graphical indicators.

The zone information may therefore comprise information for graphically associating each interactive zone to its corresponding feature. Where the interactive zones are configured to overlap the corresponding feature, the position information of the zone information provides this information.

In the previously described examples, each feature of an interventional medical device has been the interventional medical device itself. In other words, interactive zones have only been generated for interventional medical devices, e.g. and not portions or parts of an interventional medical device.

However, in some embodiments, the feature of an interventional medical device comprises a part or portion of the interventional medical device, such as a landmark of an interventional medical device. Suitable examples of landmarks for an interventional medical device would be apparent to the skilled person.

By way of example only, the feature of an interventional medical device may comprise the end or tip of the interventional medical device. In some examples, the feature of an interventional medical device is the predicted end or tip of the interventional medical device. By way of another example, the feature of an interventional medical device may comprise a (radiopaque) marker on the interventional medical device. One suitable example of the use of radiopaque markers, which could be suitable for use as a feature, is found in the FEVAR (Fenestrated Endovascular Aortic Repair) stent grafts.

By way of yet another example, the feature of an interventional medical device may comprise a particular element of the interventional medical device, such as a gate marker of a stent graft.

Other suitable examples for the feature(s) of an interventional medical device would be apparent to the skilled person.

It is not essential to generate an interactive zone for each (feature of an) interventional medical device in the image. Rather, it may be possible for only a subset of possible interactive zones to be generated.

By way of example, in some embodiments, an interactive zone may be generated for only certain, desired types (of features of) an interventional medical device. In particular, the type may be a desired type of feature and/or a desired type of interventional medical device. The desired type may be defined via a user input or other signal (e.g. provided via the user interface).

Figure 6:
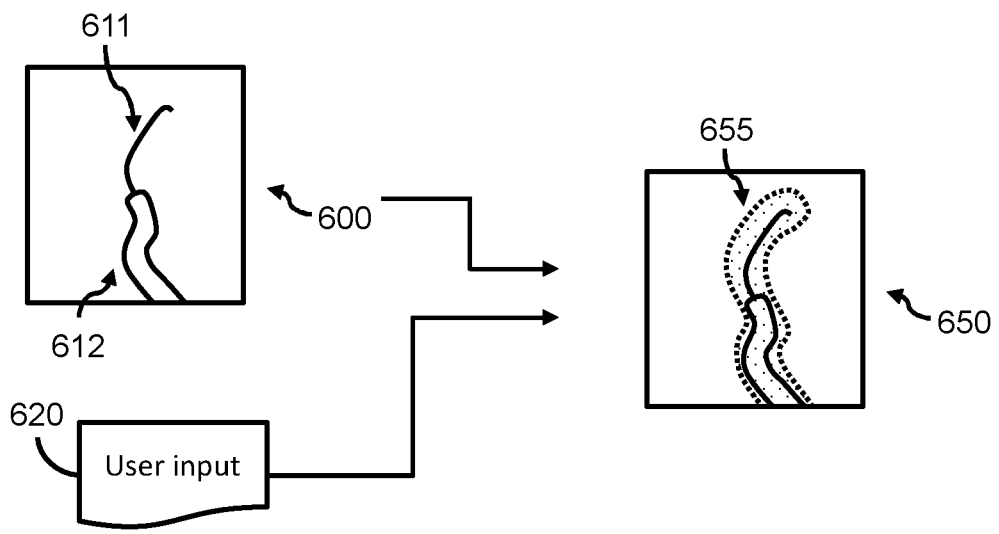

This process is illustrated in FIG. 6, in which an interactive zone is generated for an image 600 displaying two interventional medical devices of different types, a guidewire 611 and a catheter 612. A user input 620 indicates a desired type of interventional medical device (e.g. guidewires), and a single interactive zone 655 is generated for the guidewire only. Thus, the generated interactive image 650 comprises a single interactive zone 655 for the guidewire 611 (even though it may have been possible to generate more than one interactive zone).

Referring back to FIG. 2, this process may be implemented in step 203. In particular, the zone generation process may comprise receiving a user input identifying one or more desired types of interventional medical device and only generating an interactive zone for at least one feature of each identified interventional medical devices of the desired type.

The desired type may be a medical (sub-)category or label of the interventional medical device, e.g.: "guidewire", "catheter", "stent graft", "sheet" and so on. Example sub-categories may include, for example: "Davis catheter", "pigtail catheter" or "cobra catheter". Other suitable categories and sub-categories of types of an interventional medical device would be apparent to the skilled person.

However, types are not limited to such labels, but may rather comprise any category or sub-category of desired interventional medical devices. For example, devices may be categorized in two types: shape-sensed devices and non-shape sensed devices. As another example, devices may be categorized into a different two types: moving devices and non-moving (i.e. stationary) devices. As yet another example, devices may be categorized into different thicknesses (i.e. a type is a category of thickness), e.g.: <10 mm thick; >10 mm and <50 mm thick; >50 mm thick; and so on.

Thus, a "type" may be any category of the interventional medical devices, where categories can be defined using any suitable feature of the interventional medical device (e.g. shape, size, medical use/purpose, age, thickness, diameter and so on).

With continued reference to FIG. 2, the type of an interventional medical device may be obtained in step 202, e.g. by obtaining identifying information that identifies a type of each/an interventional medical device. The type obtaining process may be performed automatically, e.g. using an image recognition process, or based on external information, e.g. which identifies a type and/or identity of the interventional medical devices contained in the image.

In embodiments in which a type of the interventional medical device is identified, step 203 may further comprise, for each feature, defining one or more visual display properties (and/or values thereof) for the corresponding interactive zone, wherein features corresponding to interventional medical device(s) of a same type share a same value for a first display property (e.g. have a same color). Preferably, interactive zones for features of different interventional medical devices have a different value for the first display property (e.g. are of different colors). This aids in distinguishing between different types of features.

It will be apparent that it is not essential for the zone generation to be limited to devices of a desired type when setting different display properties for different types of the interventional medical device.

Figure 7:
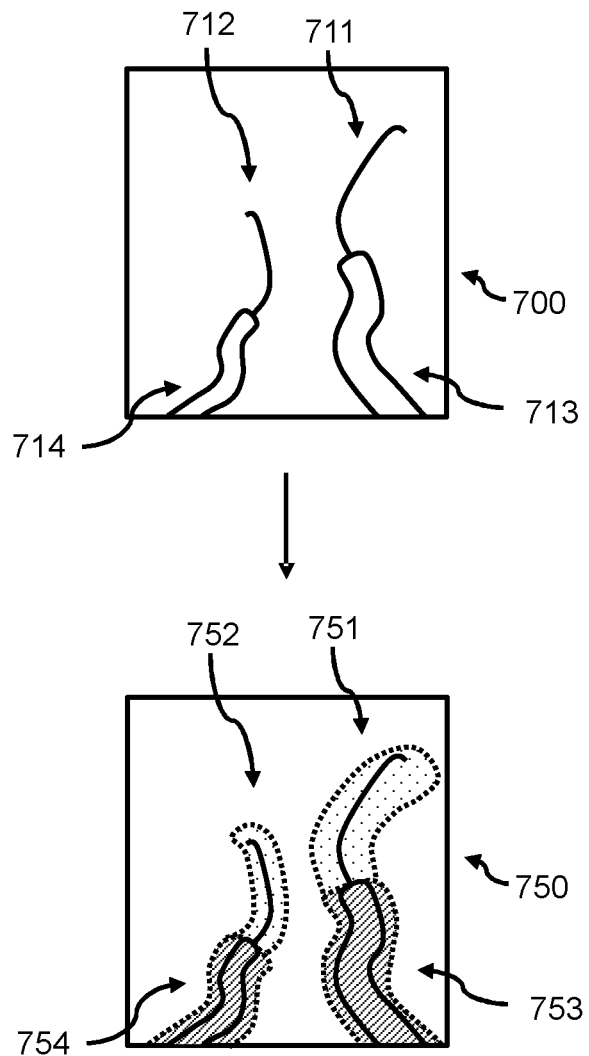

This process is illustrated in FIG. 7, in which interactive zones are generated for an image 700 displaying four interventional medical devices of two different types: a first guidewire 711; a second guidewire 712; a first catheter 713 and a second catheter 714. The first guidewire 711 and first catheter 713 are associated with one another, as are the second guidewire 712 and the second catheter 714.

In the interactive image 750, a first set of interactive zones 751, 752 are generated for the guidewires (i.e. a "first type") and a second set of interactive zones 753, 754 are generated for the catheters (i.e. a "second type"). Interactive zones in the first set, i.e. of the same type, share a same value for a display property (here, a pattern fill), as do interactive zones in the second set. However, interactive zones of different sets have different values for this display property (i.e. different types of pattern fill).

Thus, features corresponding to interventional medical device(s) of a same type share a same value for a first display property and interactive zones for features of different interventional medical devices have a different value for the first display property. This aids in distinguishing between different types of features.

As previously discussed, the zone information may be used (e.g. by a user interface processing unit) to define one or more interactive zones of an interactive image. The interactive image is provided by a user interface, which enables the user to interact with the interactive zone(s).

A user may be able to interact with an interactive zone in a number of ways, depending upon the type of user interface.

Preferably, the user interface is adapted to receive a touch and/or voice input for interaction, e.g. via a touch-screen and/or microphone (of the user interface) respectively.

To improve facilitation of a voice input, it is preferable for an interactive zone to be provided with a label when displayed. This would allow a user to interact with an interactive zone by calling out or audibly referring to the displayed label. Embodiments of generating the zone information, i.e. the zone generation process, may therefore comprise generating a unique label for each interactive zone, so as to enable the interactive zones to be distinguished from one another. The label may be arbitrary (e.g. a number) or may relate to the identity or type of the feature or the interventional medical device (e.g. "Catheter 1" or "Possible Landmark 1" or "Landmark of Catheter").

It has previously been described how interaction with an interactive zone, when displayed by a user interface, can be used to trigger one or more actions. The precise action(s) performed when interacting with an interactive zone are dependent upon implementation details, and are not considered to be essential to the concept of the invention.

An interaction zone may, for example, enable the user to interact with the system or environment to guide, tune, or visualize the interventional device or parameters thereof.

In particular, interaction with an interactive zone may trigger an action related to the feature (associated with the interactive zone) and/or the interventional medical device (associated with the interactive zone). The action may relate to an environment of the corresponding feature and/or interventional medical device, or a physical property of the feature or interventional medical device.

The triggered action may relate to the display of the feature or interventional medical device, e.g. highlighting the feature or interventional medical device, selecting the feature or interventional medical device, removing the interventional medical device from the display and so on. Selecting the feature may enable further interaction with the feature to take place, e.g. modifying parameters of the associated interventional device.

Other examples may include highlighting/outlining the selected feature or device for ease of recognition during an operation or zooming in on (an end of) the selected device for increased ease in tracking the movement of the medical device.

The triggered action may relate to the interventional medical device itself, e.g. modifying a property of the (physical) interventional medical device or automatically recording that a process involving the selected interventional medical device is taking place, e.g. to make sure that an essential device is not being removed.

Yet another response to an interaction with an interactive zone could be to modify or change the image based on the feature or interventional medical device associated with the interactive zone. For example, if the image is a part of a video comprising of a number of images, it may be possible to search for the "best" appearance of the selected device (i.e. the device associated with the interactive zone with which the user interacts) in that video, and display that image. The "best" appearance may be the image in which a contrast between the selected device and a background is the greatest.

As yet another example, a plurality of interactive zones may each correspond to possible or predicted positions of a same feature of an interventional device (e.g. a predicted tip of the interventional device). Interacting with an interactive zone may cause the corresponding position to be selected as the correct position of the feature, and the other interactive zones may be discarded. Of course, the image may be re-processed to generate new interactive zones based on this additional information.

By way of further example, the interactive image could be used to annotate the underlying image, e.g. based on a user interaction with the interactive zones, to generate ground truth data for further use to train a machine learning based algorithm. In other words, a user may interact with the interactive zone(s) to label the feature(s) of the interventional device(s) associated with the interactive zone, in order to generate a labelled image as ground truth data. This ground truth data could later be used to train a machine-learning method, such as an image segmentation algorithm or auto-labeler.

In yet other examples, an interactive image may be used to select devices whose position and properties to be recorded for automatic reporting of the operation. Thus, interaction with an interactive zone may initiate the recording of a position and/or properties of the (feature(s) of the) interventional device associated with the interactive zone.

The skilled person would therefore appreciate that a variety of different actions could be performed in response to a user interacting with an interactive zone, and further examples would be apparent to the skilled person.

It has previously been described how, in some embodiments, a machine-learning algorithm is to automatically determine the position and/or identify of features of an interventional medical device within an image. This may include, for example, automatic identification of the position (or possible positions) of an interventional medical device or predicting the position (or possible positions) of a landmark (such as a tip) of an interventional medical device.

A machine-learning algorithm is any self-training algorithm that processes input data in order to produce or predict output data. Here, the input data an image or image data and the output data comprises one or more features of an interventional medical device.

Suitable machine-learning algorithms for being employed in the present invention will be apparent to the skilled person. Examples of suitable machine-learning algorithms include decision tree algorithms and artificial neural networks. Other machine-learning algorithms such as logistic regression, support vector machines or Naïve Bayesian model are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can repeated until the error converges, and the predicted output data entries are sufficiently similar (e.g. ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

The training input data entries correspond to example images. The training output data entries correspond to corresponding example one or more features of an interventional medical device.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims.

A computer program may be stored/distributed on a suitable medium, such as an optical storage medium or a solid-state medium supplied together with or as part of other hardware, but may also be distributed in other forms, such as via the Internet or other wired or wireless telecommunication systems.

The mere fact that certain measures are recited in mutually different dependent claims does not indicate that a combination of these measures cannot be used to advantage. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method for facilitating interaction with an interventional medical device in an image for display at a user interface, the computer-implemented method comprising:
    obtaining a position of one or more features of the interventional medical device within the image for display at the user interface, the image containing a two-dimensional (2D) visual representation of the interventional medical device;
    identifying a type of the interventional medical device;
    receiving a user input indicating one or more desired types of interventional medical devices;
    if the identified type matches at least one of the one or more desired types, for each feature of the one or more features of the interventional medical device:
        determining a size and a shape for an interactive zone to overlay a portion of the image associated with the feature on the user interface, wherein the size of the interactive zone is greater than a size of the feature and is configured for interaction by a user via the user interface;
        determining a position for the interactive zone relative to the image based on the position of the feature; and
        outputting zone information comprising information on the size, the shape, and the position of the interactive zone.

2. The computer-implemented method of claim 1, wherein determining the position of the interactive zone so that the interactive zone overlaps a portion of the feature.

3. The computer-implemented method of claim 1, wherein the feature comprises the interventional medical device in entirety, or a portion of the interventional medical device, wherein the portion of the interventional medical device includes at least one of a landmark, a tip, or a component part of the interventional medical device.

4. The computer-implemented method of claim 1, wherein the shape of the interactive zone is determined to be a same shape as the feature.

5. The computer-implemented method of claim 1, further comprising processing the image to identify the position of the feature of the interventional medical device.

6. The computer-implemented method of claim 1, further comprising determining a visual display property for the interactive zone, wherein the zone information further comprises information on the determined visual display property for the interactive zone.

7. The computer-implemented method of claim 6, wherein each interactive zone overlayed on the user interface has at least one unique visual display property.

8. The computer-implemented method of claim 6, wherein the visual display property comprises a color, a shade, opacity and/or a pattern fill for the interactive zone.

9. The computer-implemented method of claim 6, herein each interactive zone associated with a feature of an interventional medical device of a different type have a different display property.

10. The computer-implemented method of claim 1, wherein the size of the interactive zone is based on a number of features in the portion of the image to be overlayed on the user interface.

11. The computer-implemented method of claim 1, wherein all the interactive zones is at least one of sized, shaped, or positioned to prevent an overlap with other interactive zones.

12. The computer-implemented method of claim 1, wherein the image comprises a medical image.

13. A non-transitory computer readable storage medium having stored a computer program comprising instructions which, when executed by a processor, cause the processor to:
    obtain a position of one or more features of an interventional medical device within an image for display at a user interface, the image containing a two-dimensional (2D) visual representation of the interventional medical device;
    identify a type of the interventional medical device;
    receive a user input indicating one or more desired types of interventional medical devices;
    if the identified type matches at least one of the one or more desired types, for each feature of the one or more features of the interventional medical device:
        determine a size and a shape for an interactive zone to overlay a portion of the image associated with the feature on the user interface, wherein the size of the interactive zone is greater than a size of the feature and is configured for interaction by the user via the user interface;

determine a position for the interactive zone relative to the image based on the position of the feature; and output zone information comprising information on the size, the shape, and the position of the interactive zone.

14. A system for facilitating interaction with an interventional medical device in an image for display at a user interface, the system comprising:

a processor configured to:

obtain a position of one or more features of the interventional medical device within the image for display at the user interface, the image containing a two-dimensional (2D) visual representation of the interventional medical device;

identify a type of the interventional medical device;

receive a user input indicating one or more desired types of interventional medical devices;

if the identified type matches at least one of the one or more desired types, for each feature of the one or more features of the interventional medical device:

determine a size and a shape for an interactive zone to overlay a portion of the image associated with the feature on the user interface, wherein the size of the interactive zone is greater than a size of the feature and is configured for interaction by a user via the user interface;

determine a position for the interactive zone relative to the image based on the position of the feature; and output zone information comprising information on the size, the shape, and the position of the interactive zone.

15. The system of claim 14, wherein the processor is further configured to determine the position of the interactive zone so that the interactive zone overlaps a portion of the feature.

16. The system of claim 14, wherein the processor is further configured to determine the shape of the interactive zone to be a same shape as the feature.

17. The system of claim 14, wherein the processor is further configured to process the image to identify the position of the feature of the interventional medical device.

18. The system of claim 14, wherein the processor is further configured to determine a visual display property for the interactive zone, wherein the zone information further comprises information on the determined visual display property for the interactive zone.

19. The system of claim 18, wherein each interactive zone overlayed on the user interface has at least one unique visual display property.

20. The system of claim 14, wherein each interactive zone associated with a feature of an interventional medical device of a different type have a different display property.

* * * * *